United States Patent [19]

Zarchy et al.

[11] Patent Number: 5,292,987
[45] Date of Patent: Mar. 8, 1994

[54] HYDROCARBON ADSORPTION AND ISOMERIZATION PROCESS

[75] Inventors: Andrew S. Zarchy, Amawalk, N.Y.; Nelson Cusher, Buffalo Grove, Ill.; Gary J. Welch, Danbury, Conn.

[73] Assignee: UOP, Des Plaines, Ill.

[21] Appl. No.: 951,060

[22] Filed: Sep. 25, 1992

Related U.S. Application Data

[63] Continuation of Ser. No. 735,559, Jul. 25, 1991, abandoned, which is a continuation-in-part of Ser. No. 571,484, Aug. 23, 1990, abandoned.

[51] Int. Cl.$^5$ .............................. C07C 5/13; C07C 7/12
[52] U.S. Cl. ........................................ 585/738; 585/820; 585/826
[58] Field of Search ........................ 585/826, 738, 820

[56] References Cited

U.S. PATENT DOCUMENTS

| | | | |
|---|---|---|---|
| 4,176,053 | 11/1979 | Holcombe | 208/310 Z |
| 4,210,771 | 7/1980 | Holcombe | 585/701 |
| 4,709,116 | 11/1987 | Zarchy et al. | 585/738 |
| 4,709,117 | 11/1987 | Gray | 585/738 |
| 4,717,784 | 1/1988 | Stem et al. | 585/738 |
| 4,831,207 | 5/1989 | O'Keefe et al. | 585/737 |

Primary Examiner—Anthony McFarlane
Assistant Examiner—Nhat Phan
Attorney, Agent, or Firm—Thomas K. McBride; John G. Tolomei; Richard P. Silverman

[57] ABSTRACT

Processes are disclosed for the adsorption and isomerization of paraffinic hydrocarbons wherein an absorption cycle is employed that utilizes a non-adsorbable purge gas for regenerating the adsorber beds, which cycle includes adsorption, regeneration and void space purging steps and wherein one of said void space purging steps comprises passing an adsorber feed to the adsorber bed to purge non-adsorbable purge gas from the void space and said step is continued until at least a portion of the non-adsorbed hydrocarbons in the adsorber feed elutes from the void space of the adsorber bed. Processes are further disclosed for sulfur and/or ammonia-containing feeds that employ additional conversion and adsorption zones to prevent the sulfur and/or ammonia compounds from contacting the isomerization catalyst. The products from the processes are useful as motor fuel blending components.

18 Claims, 3 Drawing Sheets

HYDROCARBON ADSORPTION AND ISOMERIZATION PROCESS

CROSS-REFERENCE TO RELATED APPLICATIONS

This application is a continuation of copending U.S. Ser. No. 753,559, filed Jul. 25, 1991, now abandoned, which is a continuation-in-part of U.S. Ser. No. 571,484, filed Aug. 23, 1990, now abandoned.

FIELD OF THE INVENTION

The present invention relates to octane upgrading and more particularly to separating hydrocarbon feedstreams into high and low octane fractions and optionally isomerizing the low octane fractions.

BACKGROUND OF THE INVENTION

The separation of mixtures of chemical compounds into two or more fractions by selective adsorption using molecular size adsorbents is generally known. The separation is usually effected by what is known as a relative adsorptivity separation where one component or fraction is more strongly adsorbed than another, or, a size selective separation which takes advantage of the uniform diameters of pores of a given molecular sieve adsorbent to permit the adsorption of certain compounds or fractions while essentially excluding others. The separation of normal paraffins from isoparaffins has been found to be particularly adapted to size selective adsorptive separations and a number of processes have been proposed for this purpose. Some of the processes have been based on contacting the mixed hydrocarbon feed in the vapor phase with a molecular sieve having pore diameters of about 5 Å to adsorb the straight chain hydrocarbon compounds, i.e., normal paraffins, followed by desorption of the straight chain compounds at a lower pressure or higher temperature usually with the aid of a purge gas. Other processes have used a displacement purge material which is sufficiently strongly adsorbed to exert a displacing action on the adsorbed straight chain compounds with little or no change in temperature or pressure. One process of particular interest operates under essentially isobaric and isothermal conditions and desorption is accomplished using a non-adsorbable purge gas instead of a strongly adsorbable displacement purge material. Such a process is defined in detail in U.S. Pat. No. 4,176,053, issued to Holcombe.

The above-identified patent discloses a process for separating normal paraffins from an admixture with non-normal paraffins by passing a feedstock mixture of same in the vapor state and at superatmospheric pressure periodically in sequence through each of at least four fixed beds of a system containing a zeolitic molecular sieve adsorbent having effective pore diameters of substantially 5 Å, each of said beds cylically undergoing the stages of;

(A-1) adsorption-fill, wherein the vapor in the bed void space consists principally of a non-adsorbable purge gas and the incoming feedstock forces the non-adsorbable purge gas from the bed void space out of the bed without substantial intermixing thereof with non-adsorbed feedstock fraction;

(A-2) adsorption, wherein the feedstock is cocurrently passed through the bed and the normal paraffin constituents of the feedstock are selectively adsorbed into the internal cavities of the crystalline adsorbent and the non-adsorbed constituents of the feedstock are removed from the bed as an effluent having a greatly reduced content of the normal paraffin feedstock constituents;

(D-1) void space purging, wherein the bed loaded with normal paraffins to the extent that the stoichiometric point of the mass transfer zone thereof has passed between 85 and 97% of the length of the bed and containing in the bed void space a mixture of normals and non-normals in essentially feedstock proportions, is purged countercurrently, with respect to the direction of adsorption stage (A-2), by passing through the bed a stream a non-adsorbable purge gas in sufficient quantity to remove the void space feedstock vapors; and (D-2) purge desorption, wherein the selectively adsorbed feedstock normal paraffins are recovered as a product stream by passing a non-adsorbable purge gas countercurrently with respect to adsorption stage (A-2) through the bed until the major proportion of adsorbed normals has been desorbed and the bed void space vapors consist principally of non-adsorbable purge gas.

Adsorption processes such as described above have been proven to be commercially useful and have been integrated with isomerization processes to provide a highly isomerized product that is useful as a blending component in the production of motor fuels, particularly gasoline. Such processes are known in the art as "TIP", i.e., TOTAL ISOMERIZATION PROCESS, and are described, for example, in U.S. Pat. No. 4,210,771, issued to Holcombe, 4,709,116, issued to Zarchy et al. and 4,709,117, issued to Gray Jr. Other similar adsorption/isomerization processes such as described in U.S. Pat. No. 4,717,784, issued to Stem et al., disclose the adsorption of monomethyl paraffins in addition to normal paraffins.

Generally, the TIP process comprises passing a stream containing a mixture of normal and non-normal hydrocarbons into an isomerization reactor to catalytically isomerize at least a portion of the normals in the presence of hydrogen and a catalyst composition, which typically is a zeolitic molecular sieve with a hydrogenation component. Other catalyst compostions such as alumina-base catalysts have been used as well. Since the isomerization reaction is equilibrium limited, the amount of non-normal paraffins in the feed to the isomerization reactor is minimized. The effluent from the reactor typically contains as much as 20–50 wt. % normal paraffins. The reactor effluent is partially condensed to provide a hydrogen-containing overhead which is recirculated to a main purge gas loop and a hydrocarbon liquid fraction which is passed to an adsorbent bed such as described above where the normal paraffins are selectively adsorbed and the non-normal paraffins are passed out of the adsorber as an adsorption effluent and eventually an isomerate product. The normal paraffins are then desorbed from the bed using purge gas from the main purge gas loop. The fresh feedstream can either be initially supplied to the isomerization reactor or to an adsorbent bed depending on the feedstream composition and other factors known to those skilled in the art.

Despite the usefulness of the above-described adsorption and isomerization processes, improvements are sought. In particular, it has been customary to terminate the adsorption-fill step of the adsorption cycle prior to the breakthrough of hydrocarbons into the effluent stream, i.e., when the concentration of hydrogen has dropped below the level in the non-adsorbable purge gas, e.g., below about 90 mol. %. The effluent stream, known as A-1 effluent, is rich in hydrogen and is typically recycled as purge gas to an adsorbent bed undergoing purge desorption, i.e., D-2 step. When operated in such a manner, there is still hydrogen left in the void spaces of the adsorbent bed when the adsorption fill is terminated and the adsorption step, i.e., A-2 step, is commenced. This remaining void space hydrogen is then passed out of the adsorbent bed with the adsorption effluent.

In the naphtha isomerization process or TIP process according to Holcombe ('771) or in the separation process according to Holcombe ('053), the cycles of the operation are set such that the composition of the hydrogen reaches some minimal acceptable purity level. The A-1 step was completed before any degradation of the hydrogen purity from 100 mol. %.hydrogen was observed. At the same time a layer of isoparaffins is formed behind the hydrogen layer and in front of the feed layer. In the second step, or A-2 step, the introduction of feed was continued in order to force the layer of isoparaffins from the bed. In order to maintain the 100 mol. % hydrogen purity of the A-1 effluent, it was necessary to have approximately 15 mol. % hydrogen in the A-2 effluent with the isoparaffin product. This leaves the adsorbent in the bed saturated with normal paraffins and the void spaces of the bed filled with the feed composition. During the D-1 step, hydrogen gradually displaces the normal paraffins from the adsorbent and forces the feed from the bed. In the next step, or D-2 step, the hydrogen flow is continued with the almost pure hydrogen produced during the A-1 step and the normals are withdrawn from the feed end of the bed. This material comprising predominantly hydrogen and normal paraffins becomes the feed to the isomerization reactor.

It has been found that the presence of large and varying amounts of hydrogen in the adsorption effluent, known as A-2 effluent, can be undesirable. For instance, as shown in the Drawing in both U.S. Pat. Nos. 4,176,053 and 4,210,771, the feedstream is heated by indirect heat exchange with the adsorption effluent stream. Since the adsorption effluent stream varies in composition and molecular weight throughout the adsorption cycle due to the varying presence of hydrogen, the heat content also varies. Such variations can lead to inefficient heat exchange. Moreover, the presence of hydrogen in the adsorption effluent stream can require the use of flash vessels, also shown in the Drawing of the above-identified patents, to make a phase separation and recover the hydrogen-containing vapor from the liquid product. The recovered vapor stream is typically recycled to a recycle gas compressor for further use as purge gas. The liquid product is typically passed to a stabilizer for removal of light ends, e.g., butane and lighter.

Other processes have been proposed which incorporate additional equipment to accommodate hydrogen in the adsorption effluent stream. For instance, U.S. Pat. No. 4,831,207, issued to O'Keefe et al., discloses a TIP process that incorporates an impurity removal system that is useful for preventing catalyst deactivation from sulfur or nitrogen compounds. The process utilizes a reactor system to convert the sulfur and nitrogen compounds to $H_2S$ or $NH_3$ when necessary and adsorbent beds to adsorb the $H_2S$ or $NH_3$. When processing a feedstream that contains sulfur compounds, the above-identified patent discloses that the hydrogen-containing adsorption effluent stream from the A-2 step can be employed as a desorbent for the sulfur-containing adsorber bed. The resulting adsorption effluent stream is then phase separated and the overhead therefrom contains $H_2S$ and hydrogen. Since combining the $H_2S$-containing overhead with the main purge gas loop in the TIP system could lead to sulfur poisoning of the isomerization catalyst, an additional compressor is often required to separate the recycle gas loops. The heat exchanger which exchanges heat between the thermal swing adsorber effluent and the sour hydrogen loop was oversized to anticipate a wide variation in the molecular weight and the heat capacity of the adsorber effluent during the cycle. Furthermore, since many compressors require a relatively constant supply of gas at the inlet, a surge drum can additionally be required to steady the varying hydrogen flow. A process flow scheme illustrating an additional compressor and a surge drum is set forth in FIG. 3 of the above-identified patent, equipment Nos. 243 and 237, respectively.

Accordingly, processes are sought which can reduce the amount of hydrogen in the adsorption effluent, i.e., A-2 effluent, remove the need for two separate hydrogen circuits, and thereby improve its usefulness for heat exchange purposes and avoid the need for additional process equipment.

SUMMARY OF THE INVENTION

In accordance with the present invention, a process is provided for separating paraffin fractions of a hydrocarbon feed by adsorption in an adsorber bed and regenerating the adsorber bed with non-adsorbable purge gas, e.g., hydrogen. By extending a purging step, wherein non-adsorbable purge gas is purged from void spaces within the adsorber bed by passing hydrocarbon feed therethrough, past the point of hydrocarbon breakthrough the amount of non-adsorbable purge gas in the adsorption effluent product can be reduced. Although this change effectively results in the recycling of high octane isomerized product to the isomerization reactor, the processes can reduce the amount of non-adsorbable purge gas in the adsorption effluent product from the adsorber bed, providing beneficial effects in operability and in reduction of heat exchange and compression.

In one aspect of the present invention, there is provided a cyclic adsorption process for separating an adsorber feed containing normal paraffins in the pentane and hexane carbon range and dimethyl-branched paraffins into a non-adsorbed fraction containing dimethyl-branched paraffins and an adsorbate fraction containing normal paraffins. The process includes the steps of: (a) passing a first feedstream comprising the adsorber feed in vapor phase to one of at least four adsorber beds containing adsorbent and bed void space to adsorb the adsorbate fraction and withdrawing an adsorption effluent comprising the non-adsorbed fraction; (b) passing a first purge feed comprising a non-adsorbable purge gas to the one adsorber bed wherein the void space contains a first void space gas comprising normal and dimethyl-branched paraffins, withdrawing a first purge effluent comprising the first void space gas and passing the first purge effluent to at least one other of the adsorber beds to comprise a portion of the adsorber feed; (c) passing a second purge feed comprising the non-adsorbable purge gas to the one adsorber bed to desorb the adsorbate fraction and withdrawing a desorption effluent comprising the non-adsorbable purge gas and the adsorbate fraction; and (d) passing a second feedstream comprising the adsorber feed in vapor phase to the one adsorber bed wherein the void space contains a second void space gas comprising the non-adsorbable purge gas, withdrawing a second purge effluent comprising the second void space gas, passing the second purge effluent to at least one other of the adsorber beds to comprise a portion of the non-adsorbable purge gas, and continuing the passing until a portion of the non-adsorbed fraction has eluted from the void space of the one adsorber bed.

In another aspect of the present invention, there is provided an adsorption-isomerization process for increasing the dimethyl-branched paraffin content of a hydrocarbon feed containing reactant components selected from the group consisting of normal paraffins or monomethyl-branched paraffins in the pentane and hexane carbon range or mixtures thereof. The process includes the steps of: (a) passing a reactor feed comprising hydrogen and the reactant components to an isomerization reactor to produce a reactor effluent comprising dimethyl-branched paraffins and an adsorbate fraction comprising reactant components; (b) passing a first feedstream comprising at least a portion of the effluent as an adsorber feed to one of at least four adsorber beds containing adsorbent and bed void space to adsorb the adsorbate fraction and withdrawing an adsorption effluent comprising the dimethyl-branched paraffins; (c) passing a first purge feed comprising a hydrogen-containing non-adsorbable purge gas to the one adsorber bed wherein the void space contains a first void space gas comprising the normal and dimethyl-branched paraffins, withdrawing a first purge effluent comprising the first void space gas and passing the first purge effluent to at least one other of the adsorber beds to comprise a portion of the adsorber feed; (d) passing a second purge feed comprising the hydrogen-containing non-adsorbable purge gas and a portion of said dimethyl-branched paraffins to the one adsorber bed to desorb the adsorbate fraction and withdrawing a desorption effluent comprising said hydrogen-containing purge gas and at least a portion of said dimethyl branched paraffins and the adsorbate fraction; (e) passing a second feedstream comprising the adsorber feed to the one adsorber bed wherein the void space contains a second void space gas comprising the non-adsorbable purge gas, withdrawing a second purge effluent comprising the second void space gas, passing the second purge effluent to at least one other of the adsorber beds to comprise a portion of the hydrogen-containing purge gas and continuing the passing of the second feedstream until a portion of the dimethyl-branched paraffins has eluted from the void space of the one adsorber bed; and (f) passing at least a portion of the desorption effluent to the isomerization reactor to comprise at least a portion of the reactor feed.

In still yet another aspect of the present invention, there is provided an adsorption-isomerization process for increasing the dimethyl-branched paraffin content of a hydrocarbon feed containing components selected from the group consisting of normal paraffins or monomethyl-branched paraffins in the pentane and hexane carbon range or mixtures thereof, which feed additionally contains at least sulfur and/or nitrogen components. The process includes the steps of: (a) passing the hydrocarbon feed to a catalytic reaction zone containing a catalytically effective amount of a conversion catalyst, under hydrogen sulfide and ammonia forming conditions to convert substantially all of the sulfur in the hydrocarbon feed to hydrogen sulfide and substantially all of the nitrogen in the hydrocarbon feed to ammonia and thereby produce a hydrogen sulfide and/or ammonia containing hydrocarbon feed; (b) passing the hydrogen sulfide and/or ammonia-containing hydrocarbon feed to a first adsorber bed in a first adsorption zone having at least two adsorber beds containing an adsorbent selective for the adsorption of hydrogen sulfide and ammonia to adsorb the hydrogen sulfide and/or ammonia and withdrawing a first adsorption effluent depleted in the hydrogen sulfide and/or ammonia; (c) passing a reactor feed comprising hydrogen and at least a portion of the first adsorbtion effluent to an isomerization reactor containing an isomerization catalyst which is deleteriously affected by the presence of hydrogen sulfide and/or ammonia to produce a reactor effluent comprising the dimethyl-branched paraffins and an adsorbate fraction comprising the components; (d) passing a first feedstream comprising at least a portion of the reactor effluent as an adsorber feed to a second adsorber bed in a second adsorption zone having at least four adsorber beds containing adsorbent and bed void space to adsorb the adsorbate fraction and withdrawing a second zone adsorption effluent comprising the dimethyl-branched paraffins; (e) passing a first purge feed comprising a hydrogen-containing non-adsorbable purge gas to the second adsorber bed wherein the void space contains a first void space gas comprising the normal and dimethyl-branched paraffins, withdrawing a first purge effluent comprising the first void space gas and passing the first purge effluent to at least one other adsorber bed in the second adsorption zone to comprise a portion of the adsorber feed; (f) passing a second purge feed comprising the hydrogen-containing non-adsorbable purge gas to the second zone adsorption zone to desorb the adsorbate fraction and withdrawing a second zone desorption effluent comprising the hydrogen-containing non-adsorbable purge gas and the adsorbate fraction, and at least a portion of dimethyl-branched paraffins. (g) passing a second feedstream comprising the adsorber feed to the second adsorber bed wherein the void space contains a second void space gas comprising the non-adsorbable purge gas, withdrawing a second purge effluent comprising the second void space gas, passing the second purge effluent to at least one other adsorber bed in the second adsorption zone to comprise a portion of the hydrogen-containing non-adsorbable purge gas and continuing said passing until a portion of the dimethyl-branched paraffins has eluted from the void space of the second adsorber bed; (h) passing the second zone desorption effluent to the isomerization reactor to comprise at least a portion of said reactor feed; and (i) passing at least a portion of the second zone adsorption effluent to the first adsorber bed to desorb the hydrogen sulfide and/or ammonia and provide a first zone desorption effluent comprising the dimethyl-branched paraffins and hydrogen sulfide and/or ammonia.

DETAILED DESCRIPTION OF THE INVENTION

The fresh feed treated by the processes of the present invention contains normal, monomethyl, and more highly branched paraffins. It is composed principally of the various isomeric forms of saturated hydrocarbons having from 5 to about 8, preferably 5 to 6, carbon atoms. Often, the hydrocarbon feed contains at least 40, most frequently 40 to 95 or more, weight percent of such saturated hydrocarbons. The expression "the various isomeric forms" is intended to denote all of the branched chain and cyclic forms of the hydrocarbons, i.e., non-normal, as well as the straight chain forms of the hydrocarbons, i.e., normal. Also, the prefix notations "iso" and "i" are intended to be generic designations of the non-normal forms of the hydrocarbons unless otherwise specified. As used herein, the term "adsorbate" or "adsorbate fraction" refers to the class of feed components that are adsorbed in the process of the present invention. Such adsorbates can include, for example, normal paraffins and monomethyl-branched paraffins.

The following composition is typical of a fresh feed containing 5 to 6 carbon atoms which is suitable for processing according to the invention:

| Components | Mole % |
| --- | --- |
| $C_4$ and lower | 0–7 |
| i-$C_5$ | 10–40 |
| n-$C_5$ | 5–40 |
| i-$C_6$ | 10–40 |
| n-$C_6$ | 5–30 |
| $C_7$ and higher | 0–10 |

Suitable feeds containing 5 to 6 carbon atoms are typically obtained by refinery distillation operations, and may contain small amounts of $C_7$ and even high hydrocarbons, but these are typically present, if at all, only in trace amounts. Olefinic hydrocarbons are advantageously less than about 4 mol. % in the feedstock. Aromatic and cycloparaffin molecules have a relatively high octane number. Accordingly, the preferred feeds are those which contain aromatic and cycloparaffinic hydrocarbons, e.g., at least 3, and more typically from 5 to 25 mol. % of these components combined.

In a preferred aspect, the non-cyclic $C_5$ and $C_6$ hydrocarbons typically comprise at least 60, more typically at least 75, mol. % of the feed, with at least 25, and preferably at least 35, mol. % of the feed being hydrocarbons selected from the group of isopentane, isohexanes and combinations of these. Preferably, the feed will comprise at least 5 mol. %, and, more preferably, at least 20 mol. % of a combination of n-pentane and n-hexane.

The adsorbent or adsorbents employed in the present processes for adsorbing normal paraffins can be any of the naturally occurring or synthetically produced adsorbents which will selectively, on the basis of molecular size, adsorb normal paraffins from the mixture thereof with non-normal paraffins. Since normal paraffins have a minimum cross-sectional diameter of about 5 Å, molecular sieves having pore diameters of about 5 Å are preferred for adsorbing normal paraffins in accordance with the present invention. Especially suitable are the cation forms of zeolite A which have pore diameters of about 5 Å. Zeolite A is well known in the art as a synthesized zeolite having a very large adsorption capacity and, depending on the cation species present, exhibit apparent pore diameters ranging from about 3 to about 5 Å. As prepared in the sodium cation form, zeolite A has pore diameters of about 4 Å. When 25%, preferably at least 40%, of the sodium cations are exchanged by calcium and/or magnesium cations, the effective pore diameter increases to about 5 Å. Zeolite A as used herein in the specification and claims is intended to denote the zeolite described and defined in U.S. Pat. No. 2,882,243. Other zeolitic molecular sieves which, in appropriate cation forms, have pore diameters of about 5 Å and which, although having less adsorption capacity than zeolite A, are suitably employed include zeolite T, U.S. Pat. No. 2,950,952 and the minerals chabazite and erionite.

In addition to an adsorbent suitable for adsorbing normal paraffins, the process of the present invention can employ other adsorbents having slightly larger pores when it is desired to adsorb certain low octane monomethyl-branched paraffins such as 2-methylpentane and 3-methylpentane,. One such adsorbent is ferrierite as disclosed in U.S. Pat. No. 4,717,784. Ferrierite is reported in the above-identified patent to be suitable for adsorbing monomethyl paraffins as well as normal paraffins while rejecting the higher octane dimethyl-branched paraffins. One preferred adsorbent type for adsorbing monomethyl paraffins, while excluding larger dimethyl-branched paraffins such as 2,2-dimethyl butane and 2,3-dimethyl butane, is a microporous molecular sieve having pores of an elliptical cross-section with pore dimensions between about 5.0 and 5.5 Å along the minor axis and between about 5.5 and 6.0 Å along the major axis. It is to be understood that isopentane can be adsorbed along with the other monomethyl paraffins. Since isopentane has a high octane rating unlike the monomethyl hexane paraffins, it is, in accordance with the present invention, eluted from the absorber bed along with the dimethyl-branched paraffins. That is, the adsorption step, i.e., A-2, is continued until the desired extent of isopentane has eluted from the adsorbent. An especially preferred adsorbent for use according to the present invention for adsorbing monomethyl paraffins is silicalite. Silicalite, as the term is used herein includes both the silicapolymorph disclosed in U.S. Pat. No. 4,061,724 and also the F-silicalite disclosed in U.S. Pat. No. 4,073,865 as well as variations thereof which can enhance adsorption properties such as capacity or selectivity. Other suitable adsorbents include ZSM-5, ZSM-11, ZSM-48, and other similar crystalline aluminosilicates. ZSM-5 and ZSM-11 are described in U.S. Pat. No. 3,702,866 and Re. 29,948 and U.S. Pat. No. 3,709,979, said patents being incorporated herein by reference. In general these adsorbents are high in silica content, the silica to alumina ratio being at least 10 and the preferred adsorbents are more commonly characterized as having silica to alumina ratios higher than 100.

It is to be understood that the adsorbents described above that are capable of adsorbing monomethyl paraffins may have adsorption capacity for normal paraffins as well. Nonetheless, while it is possible to adsorb both species with the larger pore adsorbent, it may be desirable to employ a 5 Å zeolite adsorbent bed upstream of a larger pore adsorbent bed so that normal paraffins can be adsorbed therein while the monomethyl paraffins can be adsorbed separately in the downstream adsorbent bed. Such a stacked bed arrangement could be contained within a single adsorbent vessel or in separate vessels.

The adsorption process of the present invention is operated at a substantially uniform temperature selected from the range of about 350°–750° F. At temperatures below about 350° F., the efficiency of a non-adsorbable purge gas which is used for desorption is decreased to the point where undesirably large quantities can be required adequately to purge the normals from the bed. Above about 750° F., the rate of coke deposition can increase rapidly and the need for more frequent oxidative regenerations of the adsorbent can arise. It is to be understood that the denomination of the present process as being "isothermal" is done so for the reason that the temperature of the feed and purge gas stream are essentially the same, i.e., within about 30° F. when entering the bed. In this, as in any adsorption-desorption cycle, it is possible for thermal gradients to develop in the bed due to heats of adsorption and desorption.

In general, the process is performed at a substantially uniform pressure, i.e., isobaric, of from about 50 to 400 psia, preferably 150 to 300 psia. The preferred pressure is dependent on the particular feedstock involved, with the higher pressures being used for the more volatile feedstocks to enhance the separation obtained and to facilitate the condensation of the product effluents. It is important that none of the adsorber feed components condense in the void space of the bed since such liquid phase material cannot be easily removed by the typical quantity of non-adsorbable purge gas alloted for void space purging.

Accordingly, the pressure is generally maintained at less than 80of the critical pressure of the highest boiling key component of the feed or less than about 60% of the dew point pressure of the feed at the process temperature, whichever is the lower value. Similarly, as in the case of the term "isothermal", the term "isobaric" is thus used to indicate that the present process does not utilize a pressure swing type of desorption and is not intended to denote that there are no pressure fluctuations. By the term "key component" used herein in conjunction with the delineation of pressure requirements is meant any paraffinic constituent of the feed mixture which is present in significant amount. As is well understood in the art, what constitutes a significant quantity of a particular component of a mixture depends somewhat on the other components present and the nature of the treatment the feed is undergoing. Generally, however in the present process, a key component will be present in an amount of about 10 mol. % or greater.

When the pressure conditions are dictated by the dew point criterion, the dew point of the hydrocarbon mixture involved can be determined by the procedure set forth in *Process Heat Transfer*, Kern, Donald Q., McGraw-Hill Book Company, New York, N.Y., at pages 319-325 inclusive. Other procedures are well known in the art to make these calculations. Routine experimentation can, of course, be resorted to, instead of calculating the dew point.

The non-adsorbable purge gas used to flush the bed void space vapors and carry from the bed desorbed paraffins in this process can be any gas or mixture of such gases which have molecular dimensions sufficiently small to enter the intracrystalline cavities of the molecular sieve, but are not themselves strongly enough adsorbed to displace the adsorbed hydrocarbons to any significant degree. Thus, it is to be understood that the term "non-adsorbable" as used herein relates to a gas that is substantially non-adsorbable relative to the particular paraffin adsorption process described herein but there may exist certain adsorption conditions or other adsorbents where purge gas may, in fact, be substantially adsorbable. Nitrogen, hydrogen, helium and methane are such materials and are preferred in the practice of this invention. Hydrogen-containing purge gases are particularly preferred because hydrogen can be effective in preventing coking of the adsorbent. Even more preferably, the purge gas is rich in hydrogen, i.e., contains more than 50 mol. % hydrogen.

The term "bed void space" for purposes of this invention is intended to mean any space in the adsorbent bed not occupied by solid material except the intracrystalline cavities of the molecular sieve crystals. The pores within any binder material which may be used to form agglomerates of the molecular sieve adsorbent is considered to be bed void space.

The paraffin adsorption process of the present invention incorporates adsorption and desorption phases. In the adsorption phase, known as the A-2 step, an adsorbate fraction in an adsorber feed containing normal paraffins and optionally monomethyl paraffins is adsorbed on the adsorbent to provide an adsorption effluent containing a non-adsorbed fraction containing non-normal hydrocarbons such as dimethyl-branched paraffins, monomethyl paraffins when not adsorbed, cyclics and aromatics. During the desorption phase, known as the D-2 step, a purge feed containing non-adsorbable purge gas is passed through the bed to desorb the adsorbate fraction and provide a desorption effluent containing the adsorbate fraction. It is to be understood that during the adsorption phase the entire adsorbate fraction is not adsorbed. For instance, a certain amount must remain in the bed void space in an equilibrium concentration with the adsorbed adsorbate. Also, a portion of the adsorbate may be allowed to elute or break through the adsorber bed into the adsorption effluent. Hence, the term "adsorbate fraction" is used to qualitatively identify the material adsorbed rather than quantitatively specify a particular segment or amount of the material adsorbed. Similarly, the term "non-adsorbable purge gas" is used to qualitatively identify the material used as the purge gas rather than specify a particular segment or amount of the purge gas.

The adsorption phase, i.e., A-2 step, wherein the normal paraffins and optionally monomethyl-branched paraffins are selectively adsorbed on the bed is continued for a period of time such that the stoichiometric point of the adsorbed hydrocarbons mass transfer zone has moved through the desired amount of the bed length. The term "mass transfer zone" as used herein has the same meaning as is generally accepted in the art, i.e., it denotes that section of the adsorber bed in which the adsorbate loading of the adsorber bed and the concentration of the adsorbate fraction in the fluid stream are both increasing with time. The term "stoichiometric point" as used herein, represents an ideal system with no mass transfer resistance and denotes a point within the mass transfer zone at which the expended capacity of the leading section of the mass transfer zone is equal to the unexpended capacity of the transfer zone. It is to be understood when monomethyl paraffins are adsorbed that the isopentane adsorption front should be allowed to break through the adsorber bed into the adsorption effluent stream along with the dimethyl paraffins. In fact, it is preferred that at least about 50 wt. %, and, most preferably, at least about 80 wt. % of the isopentane is eluted from the adsorber bed into the adsorption effluent.

In addition to the adsorption and desorption phases, there are void space purging phases. Upon completion of the A-2 adsorption step, the adsorber bed is purged in a direction countercurrent to the adsorption step with a purge gas, i.e., first purge feed, comprising the non-adsorbable purge gas, known as the D-1 step, to sweep void space gas from the adsorber bed. The effluent obtained therefrom, i.e., first purge effluent, typically contains hydrocarbons in essentially the adsorber feed composition as well as some purge gas and desorbed adsorbate, and is passed to comprise a portion of the adsorber feed and more preferably is passed in vapor phase to another adsorber bed undergoing A-2 adsorption. The extent of D-1 purging is dependent on such factors as the feed composition and the desired adsorbate purity and can be determined by those skilled in the art. As would be expected, continued D-1 purging can lead to desorption of the adsorbate fraction. Thus, the D-1 and D-2 steps can be configured, if desired, as one continuous purging step with a diversion of the desorption effluent flow as the feature distinguishing the end of D-1 and beginning of D-2. Often, however, the purge feeds for the D-1 and D-2 steps are provided at different feed rates and can have different compositions. Upon completion of the D-1 step, the adsorber bed undergoes D-2 purge desorption, as described above, wherein the selectively adsorbed adsorbate fraction is desorbed by passing a purge gas, i.e., second purge feed, comprising the non-adsorbable purge gas countercurrently with respect to A-2 adsorption through the bed until the major proportion of adsorbed paraffins has been desorbed and the bed void space vapors consist principally of non-adsorbable purge gas. In order to recover the non-adsorbable purge gas in the void space following the D-2 step, another void space purging step is performed, known as A-1 step. During the A-1 step, adsorber feed is passed to the adsorber bed wherein the incoming feed forces the non-adsorbable purge gas from the bed void space out of the bed without substantial intermixing thereof with non-adsorbed feed fraction. As used herein, the term "adsorber feed" has a qualitative meaning such as described above with respect to the terms "adsorbate fraction" and "non-adsorbable purge gas".

In the prior art, the normal operating level of hydrogen retained in the A-2 effluent was 15% which corresponded to an almost pure hydrogen composition in the A-1 effluent, and essentially no recycle of non-adsorbed product hydrocarbons into the desorption product. The present invention extends the A-1 step in order to create a recycle of these non-adsorbed product hydrocarbons.

In accordance with the present invention, the A-1 adsorption step is continued past the point of hydrocarbon breakthrough, i.e., until a portion of the non-adsorbed fraction of the feed has eluted from the void spaces of the adsorber bed. The step is preferably continued until the concentration of non-adsorbable purge gas in the effluent from a particular bed is less than 50 mol. %, more preferably less than 35 mol. % and most preferably less than 20 mol. %. It is important to note that commercial processes are often arranged to have more than one, e.g., two, beds on the A-2 step whenever there is a step change from the A-1 to the A-2 step in order to dampen the fluctuation in hydrogen concentration. Accordingly, it is not uncommon to have peak hydrogen concentrations in combined A-2 effluent streams of less than 15 mol. %, preferably less than 10 mol. % hydrogen in accordance with the present invention. The effluent is preferably passed to the purge gas loop, which comprises non-adsorbable purge gas, and preferably to a bed undergoing D-2 adsorption. The A-1 purging is preferably terminated, however, before a substantial amount of non-adsorbed hydrocarbons are passed into the effluent stream and recycled as purge gas. Excessive A-1 purging can lead to unnecessary recycle of non-adsorbed product hydrocarbons through the adsorber bed and into the desorption product, thus lowering the purity of the adsorbate in the desorption product. Moreover, when the desorption effluent is passed to an isomerization reactor as in a TIP system, excessive recycle can lead to yield loss since some cracking typically occurs in the isomerization reactor.

The adsorption effluent, i.e., A-2 effluent, can then be passed to a stabilizer to remove light hydrocarbons, e.g., $C_4$-, if desired, and then admixed with other blending components, e.g., hydrocarbon reformates, butanes, aromatics, methanol and the like, to form motor fuels such as gasoline.

In addition to the adsorption aspects of the invention, in many instances it will be advantageous to incorporate an isomerization reactor into the process to isomerize the adsorbed normal and monomethyl paraffins. The isomerization catalyst suitable for use in the process of the present invention includes all catalysts capable of isomerizing normal and monomethyl-branched paraffins to more highly branched chain paraffins. One type can be any of the various molecular sieve-based catalyst compositions well known in the art which exhibit selective and substantial isomerization activity. As a general class, such catalysts comprise the crystalline zeolitic molecular sieves having apparent pore diameters large enough to adsorb neopentane; $SiO_2/Al_2O_3$ molar ratios of greater than 3; and less than 60, preferably less than 20, equivalent percent alkali metal cations wherein those $AlO_4$ tetrahedra not associated with alkali metal cations are either not associated with any metal cation, or associated with divalent or other polyvalent metal cations. Exemplary of such zeolites are mordenite and zeolite Y.

Because the feedstock may contain some olefins and will undergo at least some cracking, the zeolitic catalyst is preferably combined with a hydrogenation catalyst component, preferably a metal of Group VIII of the Periodic Classification of the Elements (Periodic Table of the Elements, *Handbook of Chemistry and Physics*, 46th Edition, Chemical Rubber Co., 1965–1966). The catalyst composition can be used alone or can be combined with a porous inorganic oxide diluent as a binder material. Suitable catalysts of this type are disclosed in detail in U.S. Pat. Nos. 3,236,761 and 3,236,762. The disclosures of these above cited U.S. patents are incorporated herein by reference in their entireties.

Another suitable type of isomerization catalyst which may be used in this process is a composite of a metal from Group VIII of the Periodic Table with a solid support. The platinum group metals, and platinum in particular, are preferred for use as components of such a catalyst in this process. Solid supports which are suitable for a catalyst of this type include silica, alumina, magnesia, zirconia, chromia, etc. A preferred support or carrier material is alumina. It is also preferred that this type of catalyst incorporate a halogen component into the catalyst composite to impart additional acidity and activity to the catalyst. This combined halogen may be either fluorine, chlorine, iodine, bromine, or mixtures thereof. Chlorine is the most preferred halogen for purposes of the present invention and will be typically combined with the carrier material sufficient to result in a final composite that contains preferably about 0.1 to 5.0 total weight percent halogen. In addition, small amounts of halogen, such as in the form of carbon tetrachloride, may be continuously added to the catalyst to offset any halogen loss. In some instances, it may be beneficial to impregnate the catalyst with an anhydrous Friedel-Crafts type metal halide, such as aluminum chloride. Catalysts of this type are disclosed in detail in U.S. Pat. Nos. 2,999,074 and 3,772,397 and are incorporated herein by reference.

In general, the isomerization reaction can be carried out in the vapor phase when either of the two catalyst types is used, although complete vaporization does not need to be maintained when the halogenated catalyst is used. The operating temperature of the isomerization reactor is generally within the range of 100°-750° F. and, more specifically, in the range of 200°-400° F. for the halogenated catalyst and 400°-750° F. for the noble metal zeolite catalyst. The operating pressure is typically within the range of 50 to 600 psia but is not critical to the isomerization performance. However, it is generally desirable to operate the isomerization reactor in the range of 150 to 300 psia in order to be compatible with the adsorption section which preferentially operates in the range of 150 to 300 psia. The hydrocarbon flowrate through the isomerization reactor is generally maintained at a weight hourly space velocity from 0.5 to 5.0 hr.$^{-1}$, and, more typically, from 0.5 to 3.0 hr.$^{-1}$. In order to prevent catalyst coking, a hydrogen partial pressure in the range of 50 to 300 psia, and, more preferably, in the range of 100 to 200 psia should be maintained over the isomerization catalyst.

When the adsorption process of the present invention is practiced in conjunction with the isomerization process of the present invention, several configurations are possible. One configuration is known as a reactor lead process and is described in U.S. Pat. No. 4,210,771. In the reactor lead process, the feed is passed through the isomerization reactor prior to being passed through the adsorbers. Desorption effluent from the adsorbers is then combined with the feed and passed through the isomerization reactor. Another configuration is known as the adsorber lead process and is described in U.S. Pat. No. 4,709,116. In the adsorber lead process, the feed is passed through the adsorbers prior to being passed through the isomerization reactor. At least a portion of the effluent from the isomerization reactor is then combined with feed and passed through the adsorbers. A third configuration involves a split feed process wherein a portion of the feed is initially passed through the isomerization reactor, and another portion is initially passed through the adsorbers.

It will also be understood that certain combinations of adsorbent type and catalyst are preferred. For example, it is generally known that zeolite calcium A adsorbent is sensitive to acid attack. In U.S. Pat. No. 3,150,205, at column 2, lines 36 to 46, it was disclosed that:

"It is necessary that the isomerate be substantially free of hydrogen halides when charged to the adsorbent material in that the adsorbent materials useful herein are generally adversely affected and even attacked by hydrogen halides. Thus, where the isomerization process is promoted with hydrogen halide, means should be provided, as a portion of the isomerization process, for removal of hydrogen halides: a bed of alumina or other material which will react with hydrogen halides may be advantageously provided in the effluent stream from the isomerization reaction."

Accordingly, the use of halogen activated isomerization catalysts is frequently avoided when calcium A zeolite adsorbent is used unless there are appropriate means for removal of the halides as described above. One preferred combination, in accordance with the present invention, is to use a 5 Å zeolitic molecular sieve as the adsorbent and a noble metal mordenite molecular sieve as the catalyst. Another preferred combination according to the present invention is to use one of the larger pore, high silica adsorbents described supra, e.g., silicalite or ZSM-5, with a halide activated isomerization catalyst. Because of their high silica-low alumina content, adsorbents of this type possess a unique acid-resistant characteristic and removal of the halides is not always required. Another preferred combination is to use one of the larger pore, high silica adsorbents such as silicalite or ZSM-5 in conjunction with a smaller pore calcium A zeolite adsorbent as hereinbefore described with an isomerization catalyst that is not halide activated.

In another aspect of the present invention, an integrated adsorption-isomerization process is provided for sulfur and/or nitrogen-containing feeds. Many isomerization catalysts, particularly zeolitic-based molecular sieve catalysts such as platinum-containing mordenite are particularly sensitive to sulfur and/or nitrogen and can rapidly become deactivated. Thus, in order to avoid deactivation, it is essential to prevent the sulfur and/or ammonia compounds in the feeds from contacting the sulfur and or nitrogen sensitive catalysts.

U.S. Pat. No. 4,831,207, issued to O'Keefe et al. discloses such a process and is hereby incorporated by reference. Typically, the sulfur content of the feedstream will be from about 1 to 1000 ppmw when sulfur is present and the nitrogen content of the feed will be from about 0.5 to 150 ppmw when nitrogen is present. Generally, the sulfur compounds in the feedstream are converted to hydrogen sulfide and the nitrogen compounds are converted to ammonia by hydrotreating. Such a hydrotreating reaction is well known to those skilled in the art, is conventionally used in the typical hydrotreating/isomerization process, and is discussed in, for example, U.S. Pat. No. 4,533,529. Generally, the hydrogenation of the sulfur and nitrogen compounds is carried out at a temperature of from about 500° to about 650° F. depending on the conditions and the source of hydrogen chosen. Useful catalysts are those containing metals of Groups VB, VIB, VIII and the Rare Earth Series of the Periodic Table defined by Mendeleff, published as the "Periodic Table of the Elements" in Perry and Chilton, Chemical Engineers Handbook, 5th Edition. The catalysts may be supported or unsupported, although catalysts supported on a refractory inorganic oxide, such as on a silica, alumina or silica-alumina base are preferred. The preferred catalysts are those containing one or more of the metals cobalt, molybdenum, iron, chromium, vanadium, thorium, nickel, tungsten (W) and uranium (U) added as an oxide or sulfide of the metal. Typical hydrotreating catalysts include Shell 344

Co/Mo (Shell Chemical Co., Houston, Tex.), C20-5, C20-6, C20-7, C20-8 Co/Mo hydrotreating catalysts (United Catalysts, Inc., Louisville, Ky.), and the like.

The hydrogen sulfide and/or ammonia containing feedstream is then generally introduced into at least one adsorber bed in a hydrogen sulfide/ammonia adsorption zone as distinguished from the paraffin adsorption zone hereinbefore described. If desired, however, it may be advantageous at this point to cool the hydrogen sulfide/ammonia containing hydrocarbon feedstream prior to its introduction into the adsorption zone in order to enhance the effectiveness of the adsorption step.

The hydrogen sulfide/ammonia adsorbent that is used in the adsorber beds must be capable of selectively adsorbing hydrogen sulfide and/or ammonia from the hydrocarbon-containing stream and be able to withstand the temperature and pressure conditions existing within the adsorption beds. Generally, the temperature of adsorption is in the range of from about 200°–500° F., and preferably about 300°–450° F. at a pressure of about 200–700 psi. Typically at least two adsorber beds are employed although more than two can be employed if desired.

Although the temperatures within the adsorption zone are substantially similar to those in the isomerization reactor, it may still be desirable to heat the hydrogen sulfide and ammonia free hydrocarbon feedstream prior to introducing it into the reactor so as to facilitate the desired isomerization reaction temperature.

Any adsorbent may be used in this aspect of the invention as long as it is capable of selectively removing hydrogen sulfide and/or ammonia from the remaining constituents of the stream. The adsorbents which are particularly suitable in the process of this aspect of the present invention and which are capable of providing good hydrogen sulfide and/or ammonia removal at the high temperatures employed in the adsorption cycle are 4A zeolite molecular sieve and clinoptilolite.

The sulfur and/or ammonia freed feedstream is then passed to an isomerization reactor as hereinbefore described. At least a portion of the effluent from the isomerization reactor, either directly or after subsequent processing, and generally after being heated to a temperature above the sulfur and/or ammonia adsorption temperature and within the range of from about 400°–800° F., is used to regenerate the sulfur and/or ammonia loaded adsorbent beds. In the reactor-lead configuration, the isomerization reactor effluent is passed to the normal and/or monomethyl paraffin adsorption section prior to being used to regenerate the hydrogen sulfide and/or ammonia adsorbers. Thus, in this aspect of the invention, the adsorption effluent stream is ultimately used to regenerate the hydrogen sulfide and/or nitrogen adsorbers.

The process of the present invention is hereinafter described with reference to the drawings which illustrate various aspects of the present invention. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be readily discerned that the process flow depicted in the Figures may be modified in many aspects without departing from the basic overall concept of the invention. For example, the number of heat exchangers shown in the Figures has been held to a minimum for purposes of simplicity. Those skilled in the art will recognize that the choice of heat exchange configurations and methods employed to obtain necessary heating and cooling at various points within the processes is subject to engineering judgement and preference. Accordingly, there exists many possibilities for indirect heat exchange between different process streams. Depending upon specific location and circumstance of the installation of the subject process, it may also be desired to employ heat exchange against steam, hot oil, refrigerants or process streams from other processing units not shown on the Figures.

Figure 1:
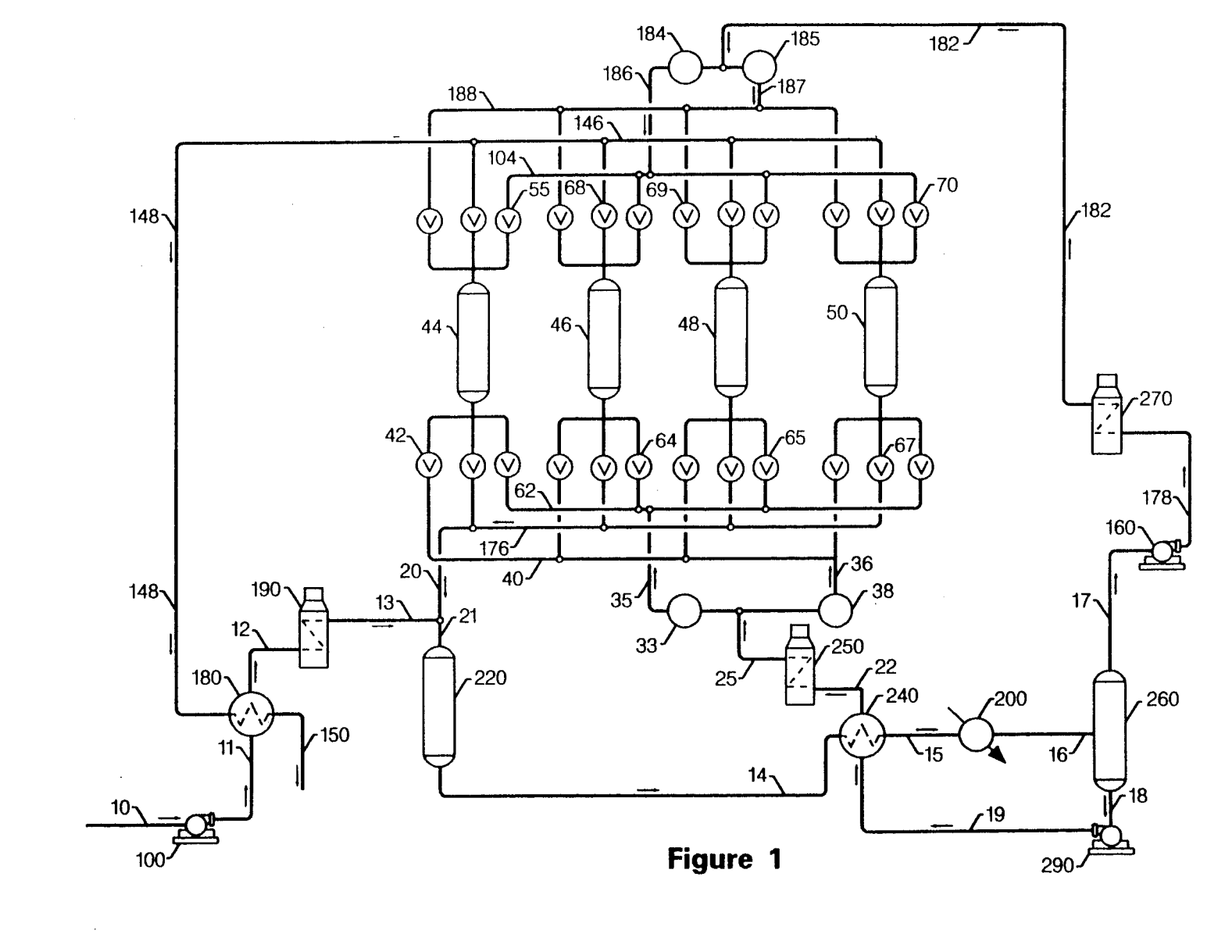
FIG. 1 is a process flow diagram of a TIP process arranged in accordance with this invention.

With reference to FIG. 1, a fresh feedstream containing normal and non-normal paraffins in primarily the pentane and hexane range with minor amounts of $C_1$–$C_4$ and $C_7$+hydrocarbons is drawn through line 10 by pump 100 and passed by line 11 to heat exchanger 180 wherein the feedstream is partially heated by indirect heat exchange with the adsorption effluent stream in line 148, the source of which is hereinafter defined. The partially heated feedstream is passed by line 12 to furnace 190 wherein the feedstream is heated to an isomerization reaction temperature of about 500° F. The heated feedstream in line 13 is combined with a desorption effluent stream from process line 20, which contains hydrogen and the source of which is hereinafter defined, and passed as a combined feed by line 21 to isomerization reactor 220 which contains a sufficient quantity of platinum-loaded mordenite isomerization catalyst to isomerize the normal paraffins. Suitable isomerization catalyst of the type described herein can be obtained from UOP, Des Plaines, Ill. The specific reaction conditions including reactor temperature, pressure, weight hourly space velocity, hydrogen partial pressure and the like are known to those skilled in the art and need not be further discussed herein.

A reactor effluent containing hydrogen, normal and non-normal hydrocarbons is withdrawn from reactor 220 by line 14, passed through heat exchanger 240 wherein it is cooled by indirect heat exchange against an adsorption zone feedstream in line 19, the source of which is hereinafter defined. The partially cooled reactor effluent is withdrawn by line 15 and further cooled in water cooler 200 and passed by line 16 to separation vessel 260.

A liquid condensate containing primarily hydrocarbons is withdrawn from separation vessel 260 by line 18, is passed through pump 290 to line 19, then through heat exchanger 240 wherein the adsorption zone feed, i.e., adsorber feed, is partially heated. The partially heated adsorption zone feed is withdrawn by line 22 and heated to the adsorption temperature of about 500° F. in furnace 250. The heated adsorption zone feed is withdrawn by line 25 and is directed partially to line 35 by way of pressure control valve 33 and partially to line 36 by means of flowrate control valve 38. Through line 36, a portion of the feed from line 25 is directed through manifold 40 and valve 42 to adsorption bed 44 undergoing A-1 adsorption. Each of the four adsorption beds in the system, mainly beds 42, 46, 48 and 50, contain a sufficient quantity of calcium zeolite A adsorbent in the form of 1/16" cylindrical pellets to adsorb normal paraffins in the adsorption zone feed. Calcium zeolite A is commercially available from a variety of sources including UOP, Des Plaines, Ill. The exact quantity of adsorbent required as well as the adsorption temperature, pressure and cycle time can be determined by one skilled in the art and need not be described in detail herein.

Bed 44, at the time that the feed passing through valve 42 enters, contains residual hydrogen-rich purge gas from the preceding desorption step. The rate of flow of the feedstream through line 36, manifold 40 and valve 42 is controlled such that bed 44 is flushed of residual purge gas uniformly over a period of about two minutes. More specifically, in accordance with the present invention, the rate of flow is controlled such that by the end of the A-1 step the effluent from bed 44 contains about 40 mol. % hydrogen with the balance consisting substantially of hydrocarbons. During this first stage of adsorption in bed 44, the hydrogen-containing purge gas effluent passes from the bed through valve 55 into manifold 104.

During the two-minute period when the purge gas was being flushed from bed 44, the remaining feedstream passes through valve 33 and line 35 through manifold 62 and valve 64 to bed 46. The normal paraffins in the feedstream are adsorbed in bed 46 which is undergoing A-2 adsorption and the non-normal paraffins emerge from the bed through valve 68 and pass through manifold 146. The non-normal paraffins, in the adsorption effluent, are then passed through line 148 to heat exchanger 180 wherein the adsorption effluent is partially cooled and then passed by line 150 out of the system as adsorption product.

It is important to note that by virtue of the present invention wherein the A-1 adsorption step is continued until a substantial portion of the hydrogen-containing purge gas is removed from the adsorber bed, it is possible to pass the adsorption effluent in line 150 as product directly to a stabilizer for removal of the butane and lighter hydrocarbons. Were it not for the present invention, it would be necessary to further cool the adsorption effluent product in line 150 and thereafter separate the cooled stream into a hydrogen-rich vapor fraction and a liquid fraction containing the adsorption effluent product which would then be sent to the stabilizer as hereinbefore described.

Moreover, although not shown in FIG. 1, adsorption processes such as described above often utilize a surge vessel on the adsorption effluent stream, e.g., line 148, in order to dampen the compositional variations, and attendant heat content variations, in the adsorption effluent stream which can range from about 90 mol. % hydrogen at the beginning of an A-2 step to about 3 mol. % hydrogen at the end of the A-2 adsorption step from a single adsorber bed and about 30-3 mol. % hydrogen when combined with A-2 effluents from other adsorber beds. By virtue of the present invention, the compositional variation in the A-2 adsorption effluent stream is substantially reduced and typically the hydrogen concentration in the adsorption effluent stream ranges from about 50 to about 3 mol. % from a single adsorber bed and far less fluctuation when combined with A-2 effluents from other adsorber beds, e.g., from about 10-3 mol. % hydrogen. As a result, the heat exchange efficiency in heat exchanger 180 can be substantially improved and thus the heat duty in furnace 190 can be reduced. The adsorption effluent stream, or a portion thereof, is particularly suitable for use as a motor fuel blending component.

During the two-minute period when the residual hydrogen is being flushed from bed 44, i.e., A-1 adsorption, bed 48 is undergoing the first stage of purging with hydrogen-rich purge gas wherein the hydrocarbons in the bed void space are being flushed from bed, i.e., D-1 purging. During the same two-minute, e.g., 10 to 3 mol. % hydrogen interval, bed 50 is undergoing the second stage of desorption, i.e., D-2 purge desorption, in which the normal hydrocarbons are desorbed from the adsorbent using the hydrogen-rich purge gas and removed from the bed. From separation vessel 260, a hydrogen-rich purge gas is withdrawn through line 17 and passed through compressor 160, line 178 and furnace 270, wherein it is heated to about 500°, and thence through line 182. By means of flow control valves 184 and 185, the gas flow from line 182 is divided into two streams, the lesser stream being passed at a sufficient rate to purge the void space of remaining adsorption feed through line 187, manifold 188, and valve 69 countercurrently (with respect to the previous adsorption stroke) through bed 48, i.e., D-1. The low controlled flowrate employed for the two-minute first stage desorption is for the purpose of flushing non-adsorbed hydrocarbons from the bed voids without causing excessive desorption of the normals from the adsorbent. The effluent from bed 48 passes through valve 65 and into manifold 62 where it is recycled through valve 64 directly to bed 46 undergoing A-2 adsorption. The major portion of the hydrogen-rich stream from line 182 is passed through control valve 184, line 186, to manifold 104 where it is mixed with the previously mentioned first stage adsorption effluent, i.e., A-1, from valve 55 and then passes through valve 70 and bed 50, i.e., D-2. During this period, selectively adsorbed normal paraffins are desorbed from the adsorbent and flushed from the bed. The effluent from bed 50 comprising hydrogen and normal paraffins passes through valve 67 and manifold 176 to line 20, where it is mixed with incoming fresh feedstream.

The foregoing description is for a single two-minute period of a total eight-minute cycle for the system. For the next two-minute period, appropriate valves are operated so that bed 44 begins A-2 adsorption, bed 46 begins D-1 purging, bed 48 begins D-2 desorption, and bed 50 begins A-1 adsorption. Similarly, a new cycle begins after each two-minute period and at the end of an eight-minute period all the beds have gone through all stages of adsorption and desorption.

The following chart indicates the functioning of each of the four beds for each two-minute period:

| Time, min. | 0–2 | 2–4 | 4–6 | 6–8 |
|---|---|---|---|---|
| Bed 44 | A-1 | A-2 | D-1 | D-2 |
| Bed 46 | A-2 | D-1 | D-2 | A-1 |
| Bed 48 | D-1 | D-2 | A-1 | A-2 |
| Bed 50 | D-2 | A-1 | A-2 | D-1 |

Those skilled in the art will recognize that cycle times and configurations other than set forth above can be employed within the process of the present invention. Cycle times, however, are generally within the range of about three to eight minutes in length, and the individual step times typically range anywhere from about 30 seconds to three minutes in length.

Figure 2:
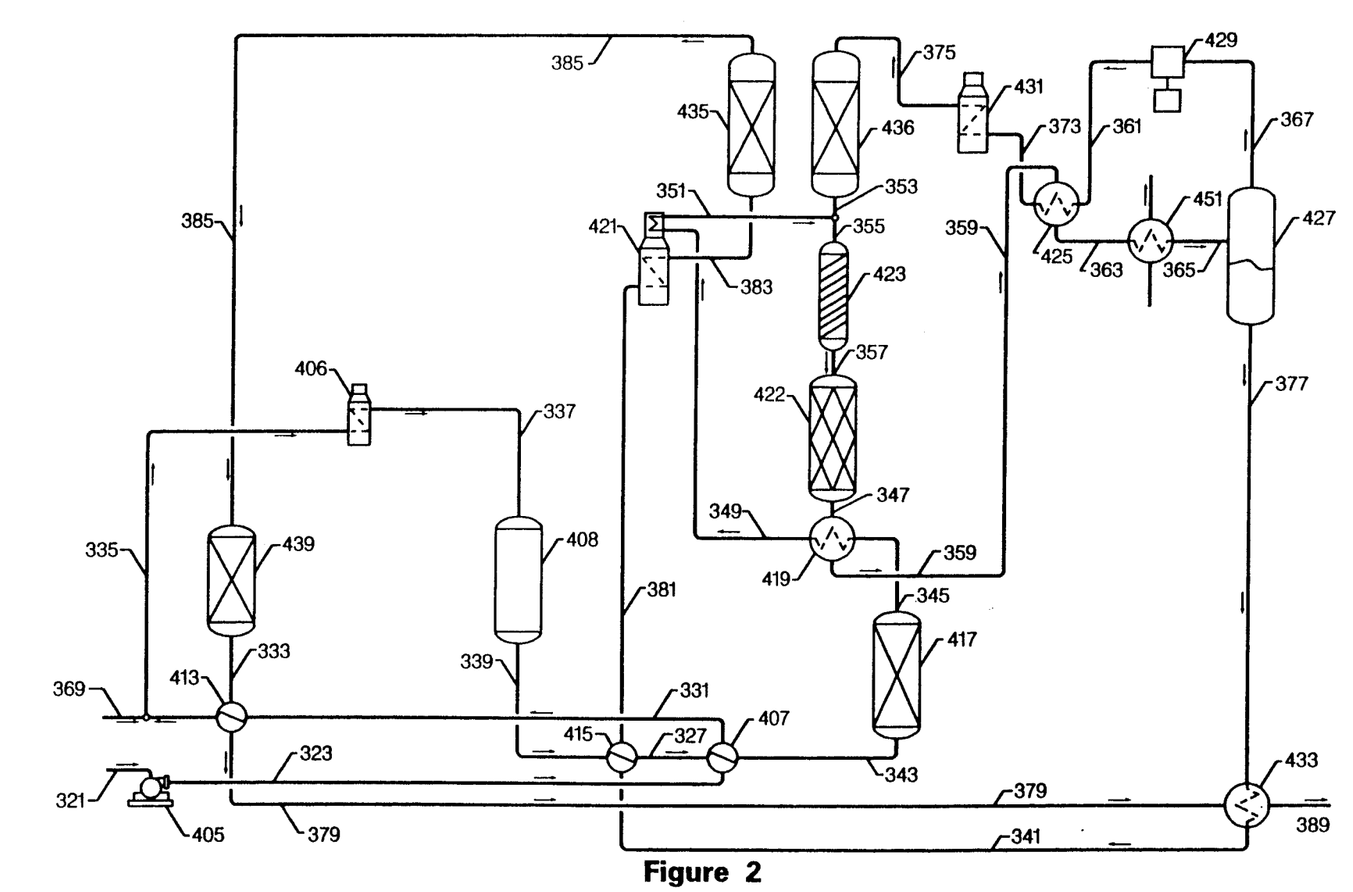
FIG. 2 is a process flow diagram of a TIP process with impurity removal capability arranged in accordance with this invention.

FIG. 2 illustrates a process flow diagram for an aspect of the invention that is useful for the adsorption and isomerization of sulfur-containing feeds. In general, the sulfur is converted to hydrogen sulfide, adsorbed in a first adsorption zone, the sulfur-free feed is then isomerized and separated in a second adsorption zone, and then the adsorption effluent from the second adsorption zone is used as a desorbent to regenerate the first adsorption zone. In FIG. 2, a total isomerization process is shown in which such sulfur removal steps are taken primarily to prevent catalyst poisoning in the isomerization reactor. Accordingly, the process shown in FIG. 2 is essentially the same as that discussed in FIG. 1 with the exception of providing these additional features. While the total isomerization process shown in FIG. 2 illustrates a reactor-lead configuration, which has been discussed earlier, it is to be understood that an adsorber-lead or a split-lead configuration is equally as applicable in the process of the present invention.

In particular, a feedstream similar to that utilized in the process shown in FIG. 1 is introduced through line 321 to pump 405 where it is first pumped to heat exchanger 407 via line 323. The feed contains sulfur compounds in the range of from about 1 to 1000 ppmw.

In heat exchanger 407, the feedstream is generally heated to a temperature in the range of from about 100° to about 250° F. by indirect heat exchange with a hydrotreater reactor effluent contained in line 327 as hereinafter defined.

Upon leaving heat exchanger 407 via line 331, the heated feed is combined with a make-up hydrogen stream contained in line 369.

The combined feedstream, thereby containing hydrogen in a sufficient quantity for converting the sulfur compounds to hydrogen sulfide, is passed via line 335 and introduced into furnace 406 and heated to a temperature of about 600° F. The vaporous feedstream leaves heater 406 via line 337 and is conveyed to hydrotreating reactor 408 in which essentially all of the sulfur and sulfur bearing compounds contained within the hydrocarbon feedstream are converted to hydrogen sulfide.

The vaporous feedstream, now containing hydrogen sulfide leaves hydrotreater 408 as a hydrotreater reactor effluent via line 339 and is passed through heat exchanger 415 so as to heat the adsorber feedstream contained in line 341, the source of which is hereinafter defined. As a result of such indirect heat exchange, the hydrotreater reactor effluent is cooled to a temperature of about 300° to about 450° F. and leaves heat exchanger 415 via line 327 to heat the fresh feedstream in heat exchanger 407. The hydrotreater reactor effluent now cooled to a temperature of about 200° to about 400° is then passed to adsorber bed 417 in a first adsorption zone 417 via line 343 in which substantially all of the hydrogen sulfide contained within the hydrotreater reactor effluent is adsorbed. The first adsorption zone is depicted in FIG. 2 as consisting of only two beds, i.e., 417 and 439 (on desorption), although any number of adsorbent beds may be utilized with some being on the adsorption mode while others are on the desorption mode.

The stream exiting the hydrogen sulfide adsorption zone via line 345 being substantially devoid of hydrogen sulfide and ammonia is the isomerization reactor feed.

This reactor feed is first heated by indirect heat exchange with a reactor effluent present in line 347 in heat exchanger 419. The reactor feed, now heated to a temperature of about 350° to about 450° F. and contained within line 349 is then further heated to the isomerization inlet temperature of about 450° to about 550° F. in a convection section of heater 421. After leaving heater 421 via line 351, the reactor feed is combined with normal hydrocarbons desorbed from adsorber beds 435 and 436 which selectively separate the normals from the non-normals as described in detail with reference to FIG. 1. Although two such adsorption beds are shown in FIG. 2, one on the adsorption mode and the other on the desorption mode, it is understood, of course, that any number of such adsorbent beds, preferably at least four, may be utilized herein. These normals which are combined with the heated reactor feed are contained within desorption effluent line 353. The combination, which forms the total reactor feed, is then passed via line 355 to a zinc oxide guard bed 423 which acts to insure that all of the sulfide compounds have been removed from the total reactor feed. This zinc oxide guard bed is merely optional and is not required in this isomerization process of the present invention. The reactor feed is then finally passed to isomerization reactor 422 via line 357. Isomerization reactor 422 is essentially identical to the isomerization reactor discussed in the process of FIG. 1.

Upon leaving isomerization reactor 422 via line 347, the reactor effluent is used to heat the isomerization reactor feed contained in line 345 in heat exchanger 419 as discussed earlier.

The cooled reactor effluent at line 359 is then further utilized to heat recycle hydrogen from line 361 in exchanger 425. The reactor effluent, containing an enhanced proportion of non-normal hydrocarbons to normal hydrocarbons in line 363, is then further cooled with air or water in heat exchanger 451 to a temperature of about 100° F. This cooled stream in line 365 is then passed to separator 427 in which the reactor effluent is flashed separating hydrogen from the hydrocarbons to form a hydrogen-rich purge gas in line 367 and a liquid condensate in line 377. The purge gas is then compressed in compressor 429, heated in heat exchanger 425 with reactor effluent as noted earlier, and is passed via line 373 to furnace 431 where it is heated to the desired desorption temperature of about 500° F. passed by line 375 to adsorber 436 which is undergoing desorption to provide the desorption effluent in line 353 as hereinbefore described.

The liquid condensate from separation chamber 427 is a mixture of non-normal and normal hydrocarbons and comprises the adsorber feed. Thus, this stream is sent to a second adsorption zone containing adsorber beds 435 and 436 in which the normals and non-normals are separated with the normals being retained by the adsorbent and the non-normal compounds being withdrawn as the product. As noted above, the normals are adsorbed and recycled back to the isomerization reactor such that the normals are recycled to extinction and a high octane product is achieved.

The adsorber feed in line 377 is first heated with unstabilized isomerate product contained in line 379 in heat exchanger 433 and is then passed on to heat exchanger 415 in line 341 as discussed earlier.

After leaving heat exchanger 415 at line 381, the adsorber feed is heated in furnace 421 to the normal/non-normal separation temperature of about 500° F. This heated stream is then sent to adsorbent bed 435 via line 383 in which normal hydrocarbons are selectively adsorbed by the adsorbent contained therein by the adsorption cycle of the present invention previously described in detail herein.

The non-normal hydrocarbons pass through adsorbent bed 435 into line 385 and comprise the adsorption effluent stream. This stream is the product stream from the total isomerization process and is then used to desorb the hydrogen sulfide contained within the hydrogen sulfide adsorption zone, i.e., first adsorption zone, which had been on a previous adsorption step.

Accordingly, the adsorption effluent is used to desorb hydrogen sulfide contained within adsorption zone 439 to produce a product desorption effluent in line 333. This product desorption effluent, now containing hydrogen sulfide is then heat exchanged against fresh feed in heat exchanger 413. It is then passed by line 379 and utilized to heat adsorber feed in heat exchanger 433 and is thereafter removed as a product from the process by line 389.

As noted above with reference to FIG. 1, because the adsorption effluent stream in line 385 consists substantially of hydrocarbons and has only a small amount, e.g., less than about 2 mol. % of hydrogen, it is not necessary to further cool and condense the hydrocarbon fraction so that the hydrogen fraction, which would otherwise be present, could be saved. Thus, the final product desorption effluent stream in line 389 can be passed directly to a stabilizer, if desired, to remove the $C_4$-fraction. In addition, because it is not necessary to recover the small amount of hydrogen remaining in the product desorption effluent stream, it is further unnecessary to recompress the hydrogen and recycle it back to the hydrogen loop. In conventional processes wherein the hydrogen contained in the product desorption effluent stream, i.e., A-2 effluent, is recovered, compressed and recycled to the hydrogen loop, such as in above cited U.S. Pat. No. 4,831,207, it is often necessary to provide a separate compressor for this purpose since the hydrogen-containing gas would typically also contain hydrogen sulfide. Accordingly, it would not be feasible in many instances to pass the contaminated hydrogen-containing gas through the main hydrogen recycle compressor, i.e., compressor 429, since the gas would ultimately find its way to the isomerization reactor 422 and deactivate the isomerization catalyst. Hence, the present invention provides an improvement over conventional processes for the reasons stated above.

The preceding description of FIGS. 1 and 2 was provided for illustrative purposes and was not intended to limit, in any way, the scope of the claims that follow.

EXAMPLE I

Prior Art Operation

A pilot plant consisting of two adsorber beds each containing 100 grams of a 5 Å zeolite molecular sieve adsorbent and associated heaters, surge drums and heat exchangers was used to experimentally determine the performance of the adsorber system for variations in the composition of the A-2 effluent. The arrangement of the adsorber vessels and heat exchangers represented a small-scale version of a commercial unit. A mixed hydrocarbon feedstock comprising hydrocarbons in the $C_5$–$C_6$ range was charged to an adsorber bed at a temperature of 500° F. and a pressure of 250 psig. Forty percent of the $C_5$'s were normal pentane and 20% of the $C_6$'s were normal hexane. Process cycle times for the adsorption and desorption times were set according to similar commercial cycle times. The split between A-1 and A-2 was achieved by varying the flowrate of A-1 during a fixed total adsorption time.

Figure 3:
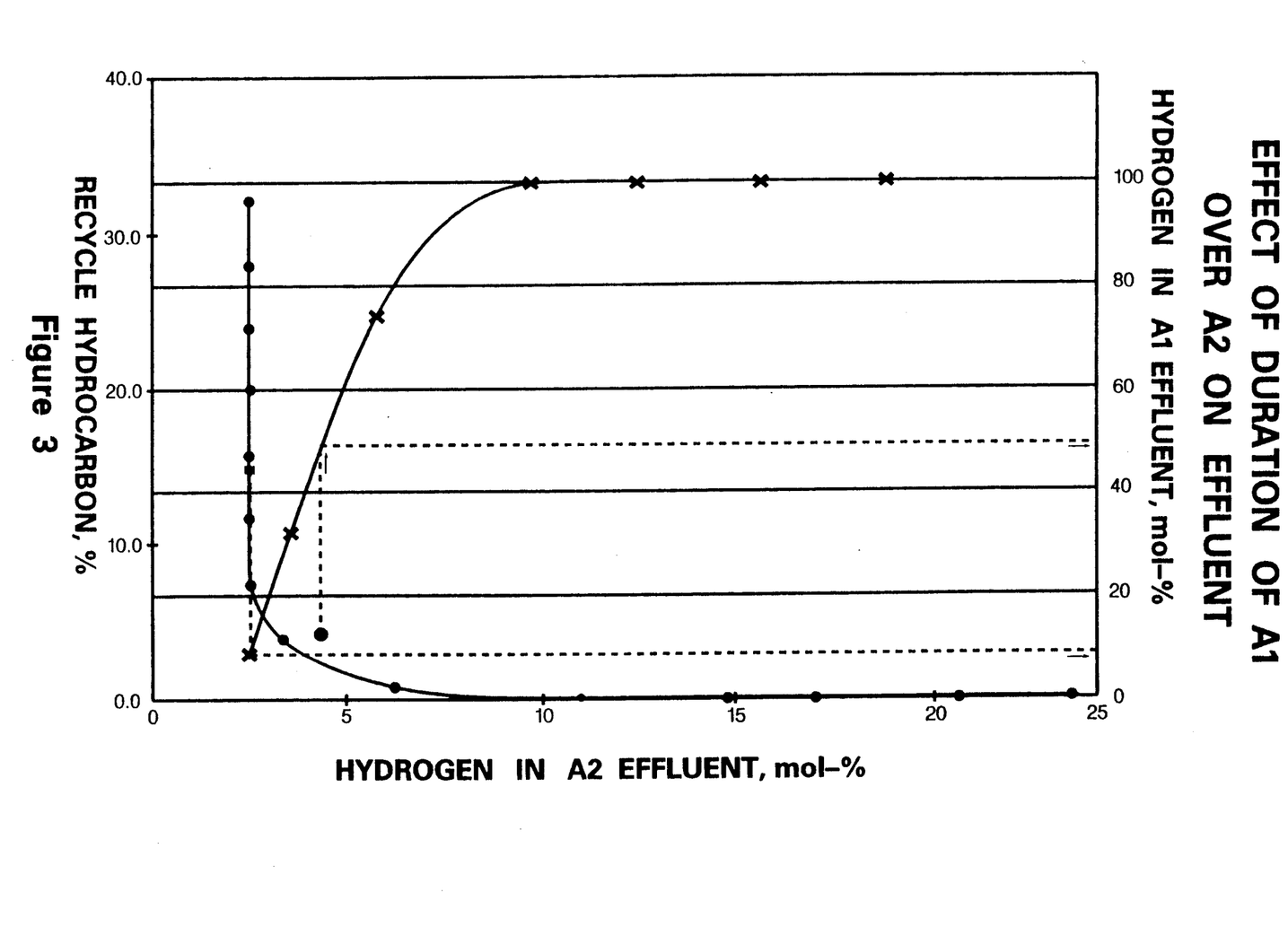
FIG. 3 is a diagram showing the effect of the continuation of the A-1 step in relation to the A-2 step in the adsorption process of the prior art and this invention.

Referring to FIG. 3, showing the effect of the duration of the A-1 over the A-2 step on effluent breakthrough, there are two main curves plotted. The first curve whose points are indicated with an X represents pilot plant data for the adsorption of normal paraffins and indicates the hydrogen purity (right-hand axis) in the A-1 stream. The second major line is shown as circles and indicates the percent hydrocarbon in the A-1 effluent stream (left-hand axis). The recycle percentage plotted in FIG. 3 is determined on a weight basis and calculated as follows:

$$\frac{\text{Hydrocarbons in A-1 Effluent} \times 100\%}{(\text{Fresh Feed} + \text{Hydrocarbond in D-2 Effluent})}$$

This data illustrates the operation of the process according to Holcombe ('053) and ('771) and O'Keefe ('207) and provide the basis for the operating philosophy which guided that operation. As shown in FIG. 3, a hydrogen composition of 15% in the A-2 effluent corresponded to an almost pure hydrogen composition in the A-1 effluent and thus corresponded to no recycle of non-adsorbed hydrocarbons in the A-1 effluent.

In two separate commercial field tests of TIP units presented below which had been operating in the method according to Holcombe, the operation was adjusted by changing the cycle times and the A-1 flow in order to approximate the process of the current invention. Prior to the tests, both plants normally operated at 15 mol. % hydrogen in the A-2 effluent, which resulted in no hydrocarbon recycle and a purge gas or A-1 effluent hydrogen purity in the 99+mol. % range.

EXAMPLE II

In a first commercial operation, the unit was processing a $C_4$–$C_7$ mixed hydrocarbon feed at a rate of 7,500 barrels per day. The operating conditions, adsorbent, and product octane quality were the same as the Example II. The solid square data point on FIG. 3 shows that at 4 mol. % hydrogen in the A-2 effluent, the recycle hydrocarbons in the A-1 effluent was 15 wt. % and the hydrogen purity of the A-1 effluent (reading the upper $H_2$ purity curve at 4% $H_2$ in the A-2 effluent) was 5 mol. % at the end of the A-1 step.

EXAMPLE III

In a second commercial example processed 4,000 barrels per day of a mixture of $C_4$–$C_7$ hydrocarbons. The system consisted of 4 adsorber beds containing a 5 Å zeolite molecular sieve adsorbent. The unit was producing an 88 research octane ($C_5$+basis) gasoline blending component. The adsorption temperature was held constant at 500° F. and the pressure at the feedpoint was 275 psig. The data representing this operation is shown on FIG. 3 as the solid dot. At approximately 6% hydrogen in the A-2 effluent, the system had 5% recycle hydrocarbons in the A-1 effluent and the hydrogen in the purge gas was 50% at the end of the A-1 step as indicated in the effluent $H_2$ purity curve for 6% $H_2$ in the A-2 effluent.

In Example II a test was made to remove as much of the hydrogen from the A-2 effluent as possible. By reducing the hydrogen purity of the A-1 effluent from 100 to 5 mol. %, the hydrogen in the A-2 effluent was reduced from 15 to 4 mol. % hydrogen. At these conditions the variations in molecular weight of the A-2 effluent which averaged 65 lb/lb mol., were reduced from ±30% to ±10%. It was discovered that the reduction in the amount of hydrogen in the A-2 effluent improved the heat capacity of the A-2 effluent and subsequently improved the heat recovery of the process. It was further discovered that the isomerate product did not require separation to remove excess hydrogen before subsequent processing. However, the 16% recycle of isomerized product to the isomerization reactor resulted in corresponding capacity inefficiencies.

In Example III the reduction of the amount of hydrogen in the A-2 effluent was from 15 to 6 mol. %. This provided a more efficient operation with improved heat recovery similar to Example II. Similar benefits also were observed in the reduction of molecular weight variations of the A-2 effluent from ±30% to ±15% about an average molecular weight of 65 lb/lb mol. The purity of the hydrogen in the A-1 effluent was reduced from 100 to 50%, corresponding to a 5% recycle of non-absorbed components, such as monomethyl and dimethyl-branched hydrocarbons, to the isomerization reactor. Furthermore, the isomerized product did not require removal of excess hydrogen before subsequent processing.

Both Examples II and III demonstrated improved heat recovery and more stable operation according to the process of this invention.

It will be understood by those skilled in the art that many variations of the above described examples are possible within the scope of the present invention. For example, the range of purity of the hydrogen in the A-1 effluent may be varied to correspond to a range of hydrogen concentrations in the A-2 effluent.

We claim:

1. An adsorption-isomerization process for increasing the dimethyl-branched paraffin content of a hydrocarbon feed containing reactant components selected from the group consisting of normal paraffins or monomethyl-branched paraffins in the $C_5$-$C_6$ carbon range or mixtures thereof, said process comprising the steps of:
   (a) passing a reactor feed comprising hydrogen and said reactant components to an isomerization reactor to produce a reactor effluent comprising dimethyl-branched paraffins and an adsorbate fraction comprising said reactant components;
   (b) passing a portion of an adsorber feed comprising at least a portion of said reactor effluent as a first feedstream to a first adsorber bed in an adsorption zone comprising at least four adsorber beds containing adsorbent and bed void space to adsorb said adsorbate fraction and withdrawing an adsorption effluent comprising said dimethyl-branched paraffins from said first adsorber bed;
   (c) passing a first purge feed comprising a hydrogen-containing non-adsorbable purge gas to said first adsorber bed wherein the void space contains a first void space gas comprising said reactant components and dimethyl-branched paraffins, withdrawing a first purge effluent comprising said first void space gas from said first adsorber bed and passing said first purge effluent to at least one other of said adsorber beds to comprise a portion of said adsorber feed;
   (d) passing a second purge feed comprising said hydrogen-containing non-adsorbable purge gas and a portion of said dimethyl-branched paraffins to said first adsorber bed to desorb said adsorbate fraction and withdrawing a desorption effluent comprising said hydrogen-containing purge gas, at least a portion of said dimethyl-branched paraffins, and said adsorbate fraction from said first adsorber bed;
   (e) passing a second feedstream comprising a portion of said adsorber feed to said first adsorber bed wherein the void space contains a second void space gas comprising said non-adsorbable purge gas from said first adsorber bed, withdrawing a second purge effluent comprising said second void space gas from said first adsorber bed, passing said second purge effluent to at least one other of the adsorber beds to comprise a portion of said hydrogen-containing purge gas, and continuing said passing of said second purge effluent until a portion of said dimethyl-branched paraffins has eluted from the void space of said first adsorber bed such that the concentration of said hydrogen-containing purge gas in said second purge effluent is less than 90 mol. %; and
   (f) passing at least a portion of said desorption effluent to the isomerization reactor to comprise at least a portion of said reactor feed.

2. The process of claim 1 comprising continuing passing said second feedstream during step (e) until the concentration of hydrogen in said second purge effluent is less than 50 mol %.

3. The process of claim 2 wherein the concentration of hydrogen is less than 35 mol %.

4. The process of claim 3 wherein the concentration of hydrogen is less than 20 mol %.

5. The process of claim 1 wherein said reactant components comprise normal paraffins and said adsorption effluent further comprises isopentane.

6. The process of claim 1 wherein said adsorbate fraction comprises isopentane and the passing of said first feedstream during step (b) is continued until a substantial portion of said isopentane has eluted from said first adsorber bed.

7. The process of claim 1 which is operated in an adsorber lead configuration wherein the adsorber feed comprises said hydrocarbon feed.

8. The process of claim 1 which is operated in a reactor lead configuration wherein the reactor feed comprises said hydrocarbon feed.

9. The process of claim 1 further comprising admixing at least a portion of the adsorption effluent with other blending components to form a motor fuel.

10. The process of claim 1 wherein said desorption effluent comprises dimethyl-branched paraffins.

11. An adsorption-isomerization process for increasing the dimethyl-branched paraffin content of a hydrocarbon feed containing components selected from the group consisting of normal paraffins or monomethyl-branched paraffins in the $C_5$-$C_6$ carbon range or mixtures thereof, which feed additionally contains at least sulfur and/or nitrogen components, said process comprising:
   (a) passing said hydrocarbon feed to a catalytic reaction zone containing a catalytically effective amount of catalyst, under hydrogen sulfide and ammonia forming conditions to convert substantially all of the sulfur in the hydrocarbon feed to hydrogen sulfide and substantially all of the nitrogen in the hydrocarbon feed to ammonia and thereby produce a hydrogen sulfide and/or ammonia containing hydrocarbon feed;
   (b) passing said hydrogen sulfide and/or ammonia-containing hydrocarbon feed to a first adsorber bed in a first adsorption zone having at least two adsorber beds containing adsorbent selective for the adsorption of hydrogen sulfide and ammonia to adsorb said hydrogen sulfide and/or ammonia and withdrawing a first adsorption effluent depleted in said hydrogen sulfide and/or ammonia;

(c) passing a reactor feed comprising hydrogen and at least a portion of said first adsorption effluent to an isomerization reactor containing an isomerization catalyst which is deleteriously affected by the presence of hydrogen sulfide and/or ammonia to produce a reactor effluent comprising said dimethyl-branched paraffins and an adsorbate fraction comprising said components;

(d) passing a portion of an adsorber feed comprising at least a portion of said reactor effluent as a first feedstream to one adsorber bed in a second adsorption zone having at least four adsorber beds containing adsorbent and bed void space to adsorb said adsorbate fraction and withdrawing a second zone adsorption effluent comprising said dimethyl-branched paraffins;

(e) passing a first purge feed comprising a hydrogen-containing non-adsorbable purge gas to the one adsorber bed in the second adsorption zone wherein the void space contains a first void space gas comprising said reactant components and dimethyl-branched paraffins, withdrawing a first purge effluent comprising said first void space gas and passing said first purge effluent to at least one other adsorber bed in the second adsorption zone to comprise a portion of said adsorber feed;

(f) passing a second purge feed comprising said hydrogen-containing non-adsorbable purge gas and a portion of said dimethyl-branched paraffins to the one adsorber bed in the second adsorption zone to desorb said adsorbate fraction and withdrawing a second zone desorption effluent comprising said hydrogen-containing non-adsorbable purge gas, said adsorbate fraction, and at least a portion of dimethyl-branched paraffins;

(g) passing a second feedstream comprising a portion of said adsorber feed to the one adsorber bed in the second adsorption zone wherein the void space contains a second void space gas comprising said non-adsorbable purge gas, withdrawing a second purge effluent comprising said second void space gas, passing said second purge effluent to at least one other adsorber bed in the second adsorption zone to comprise a portion of said hydrogen-containing non-adsorbable purge gas and continuing said passing of said second purge effluent until a portion of said dimethyl-branched paraffins has eluted from the void space of the one adsorber bed in the second adsorption zone until the concentration of the hydrogen in said second purge effluent is less than 90 mol. %;

(h) passing said second zone desorption effluent to the isomerization reactor to comprise at least a portion of said reactor feed; and (i) passing at least a portion of said second zone adsorption effluent without recovering said hydrogen-containing, non-adsorbable purge gas to said first adsorber bed to desorb said hydrogen sulfide and/or ammonia and provide a first zone desorption effluent comprising said dimethyl-branched paraffins and hydrogen sulfide and/or ammonia.

12. The process of claim 10 comprising continuing passing said first feedstream during step (d) until the concentration of hydrogen in said second purge effluent of step (g) is less than 50 mol. %.

13. The process of claim 11 wherein the concentration of hydrogen is less than 35 mol. %.

14. The process of claim 12 wherein the concentration of hydrogen is less than 20 mol. %.

15. The process of claim 11 wherein said reactant components comprise normal paraffins said second zone adsorption effluent further comprises isopentane.

16. The process of claim 11 wherein said adsorbate fraction comprises isopentane and the passing of said first feedstream during step (d) is continued until a substantial portion of said isopentane has eluted from the adsorber bed.

17. The process of claim 10 which is operated in an the absorber lead configuration wherein the adsorber feed comprises said hydrocarbon feed.

18. The process of claim 10 which is operated in a reactor lead configuration wherein the reactor feed comprises said hydrocarbon feed.

* * * * *